(12) United States Patent
Alvaro et al.

(10) Patent No.: US 8,093,255 B2
(45) Date of Patent: Jan. 10, 2012

(54) IMIDAZO[1,2-A]PYRIMIDINES AS OREXIN RECEPTOR ANTAGONISTS

(75) Inventors: Giuseppe Alvaro, Verona (IT); David Amantini, Verona (IT); Sandro Belvedere, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 224 days.

(21) Appl. No.: 12/576,331

(22) Filed: Oct. 9, 2009

(65) Prior Publication Data

US 2010/0160344 A1    Jun. 24, 2010

Related U.S. Application Data

(60) Provisional application No. 61/103,969, filed on Oct. 9, 2008.

(51) Int. Cl.
 *A01N 43/90* (2006.01)
 *A61K 31/519* (2006.01)
 *C07D 487/00* (2006.01)

(52) U.S. Cl. .................. 514/259.1; 544/281

(58) Field of Classification Search .............. None
See application file for complete search history.

(56) References Cited

FOREIGN PATENT DOCUMENTS

| | | |
|---|---|---|
| EP | 849361 A2 | 6/1998 |
| EP | 875565 A2 | 11/1998 |
| EP | 875566 A2 | 11/1998 |
| EP | 893498 A2 | 1/1999 |
| WO | WO 92/01810 A1 | 2/1992 |
| WO | WO 96/34877 A1 | 11/1996 |
| WO | WO 03/002561 A | 1/2003 |
| WO | WO 03/002561 A1 | 1/2003 |
| WO | WO 2009/003993 A | 1/2009 |
| WO | WO 2009/003997 A | 1/2009 |

OTHER PUBLICATIONS

Sakurai, et al., *Cell*, 92(4): 573-585 (1998).
Bowen, et al., *Trends Pharmacol. Sci.*, 16(12): 413-417 (1995).
Cheng, et al., *Biochem. Pharmacol.*, 22(23): 3099-3108 (1973).

*Primary Examiner* — Jeffrey Murray
(74) *Attorney, Agent, or Firm* — Kathryn L. Sieburth; John Lemanowicz

(57) ABSTRACT

This invention relates to imidazopyrimidine substituted piperidine derivatives and their use as pharmaceuticals.

17 Claims, No Drawings

IMIDAZO[1,2-A]PYRIMIDINES AS OREXIN RECEPTOR ANTAGONISTS

This application claims the benefit of U.S. Provisional Application No. 61/103,969, filed Oct. 9, 2008.

FIELD OF THE INVENTION

This invention relates to imidazopyrimidylmethyl substituted piperidine derivatives and their use as pharmaceuticals.

BACKGROUND OF THE INVENTION

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; nausea and vomiting; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegenerative disorders, which includes nosological entities such as disinhibition-dementia-parkinsonism-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see *Cell*, 1998, 92, 573-585.

There is a significant incidence of obesity in westernised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metfoi in causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

SUMMARY OF THE INVENTION

WO03/002561 discloses N-aroyl cyclic amine derivatives as orexin antagonists. Compounds disclosed in WO03/002561 include piperidine derivatives substituted at the 2-position with bicyclic heteroarylmethyl groups. We have now unexpectedly found that some piperidine derivatives which are substituted at the 2-position with an imidazopyrimidylmethyl group have surprisingly beneficial properties including, for example, increased oral bioavailability and significantly increase solubility in physiologically relevant media compared to the prior art compounds. Such properties make these imidazopyrimidylmethyl substituted piperidine derivatives very attractive as potential pharmaceutical agents which may be useful in the prevention or treatment of obesity, including obesity observed in Type 2 (non-insulin-dependent) diabetes patients, sleep disorders, anxiety, depression, schizophrenia, drug dependency or compulsive behaviour. Additionally these compounds may be useful in the treatment of stroke, particularly ischemic or haemorrhagic stroke, and/or blocking the emetic response, i.e. useful in the treatment of nausea and vomiting.

Accordingly the present invention provides a compound of formula (I)

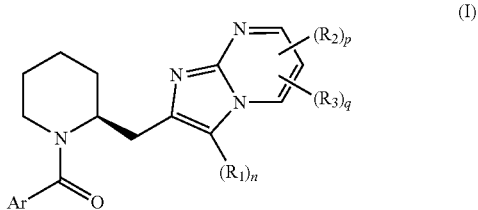

where Ar is selected from the group consisting of formula:

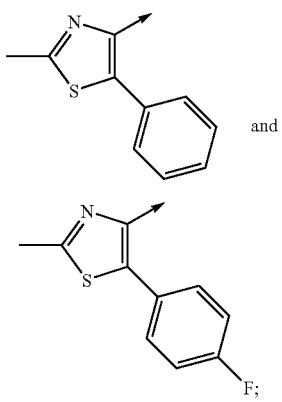

$R_1$ is $(C_{1-4})$alkyl, halo, halo$(C_{1-4})$alkyl, $(C_{1-4})$alkoxy, halo$(C_{1-4})$alkoxy, $(C_{1-4})$alkyl-O—$(C_{1-4})$alkyl, CN, $NR^5R^6$ wherein $R^5$ is H or $(C_{1-4})$alkyl and $R^6$ is H or $(C_{1-4})$alkyl;

$R_2$ is $(C_{1-4})$alkyl, halo, halo$(C_{1-4})$alkyl, $(C_{1-4})$alkoxy, halo$(C_{1-4})$alkoxy, $(C_{1-4})$alkyl-O—$(C_{1-4})$alkyl, CN, $NR^7R^8$ wherein $R^7$ is H or $(C_{1-4})$-alkyl and $R^8$ is H or $(C_{1-4})$-alkyl;

$R_3$ is $(C_{1-4})$alkyl, halo, halo$(C_{1-4})$alkyl, $(C_{1-4})$alkoxy, halo$(C_{1-4})$alkoxy, $(C_{1-4})$alkyl-O—$(C_{1-4})$alkyl, CN, $NR^9R^{10}$ wherein $R^9$ is H or $(C_{1-4})$-alkyl and $R^{10}$ is H or $(C_{1-4})$-alkyl;
n is 0 or 1;
p is 0 or 1; and
q is 0 or 1;
with the proviso that p and q are not both 0;
or a pharmaceutically acceptable salt thereof.

DETAILED DESCRIPTION OF THE INVENTION

In one embodiment Ar is a group of formula (II).
In another embodiment Ar is a group of formula (III).
In one embodiment Ar is a group of formula (II) and n is 0.
In one embodiment Ar is a group of formula (II) and n is 1.
In another embodiment Ar is a group of formula (II), n is 1 and $R_1$ is halogen.
In a further embodiment Ar is a group of formula (II), n is 1 and $R_1$ is chlorine.
In a still further embodiment Ar is a group of formula (II), n is 1, p is 1, q is 0, $R_1$ is chlorine and $R_2$ is methyl.
In one embodiment Ar is a group of formula (II), n is 0, p is 1, q is 0 and $R_2$ is methyl.
In one embodiment Ar is a group of formula (II), n is 0, p is 1, q is 1 and one of $R_2$ and $R_3$ is halo and the other is $(C_{1-4})$-alkyl.

In one embodiment Ar is a group of formula (II), n is 0, p is 1, q is 1, $R_2$ is halo and $R_3$ is $(C_{1-4})$-alkyl.
In another embodiment Ar is a group of formula (II), n is 0, p is 1, q is 1, $R_2$ is chloro and $R_3$ is methyl.
In one embodiment Ar is a group of formula (III) and n is 0.
In one embodiment Ar is a group of formula (III) and n is 1.
In another embodiment Ar is a group of formula (III), n is 1 and $R_1$ is halogen.
In a further embodiment Ar is a group of formula (III), n is 1 and $R_1$ is chlorine.
In a still further embodiment Ar is a group of formula (III), n is 1, p is 1, q is 0, $R_1$ is chlorine and $R_2$ is methyl.
In one embodiment Ar is a group of formula (III), n is 0, p is 1, q is 0 and $R_2$ is methyl.
In one embodiment Ar is a group of formula (III), n is 0, p is 1, q is 1 and one of $R_2$ and $R_3$ is halo and the other is $(C_{1-4})$-alkyl.
In one embodiment Ar is a group of formula (III), n is 0, p is 1, q is 1, $R_2$ is halo and $R_3$ is $(C_{1-4})$-alkyl.
In another embodiment Ar is a group of formula (III), n is 0, p is 1, q is 1, $R_2$ is chloro and $R_3$ is methyl.

Examples of the compounds of the invention include:
7-methyl-2-({(2S)-1-[(2-methyl-5-phenyl-1,3-thiazol-4-yl)carbonyl]-2-piperidinyl}methyl)imidazo[1,2-a]pyrimidine;
3-chloro-7-methyl-2-({(2S)-1-[(2-methyl-5-phenyl-1,3-thiazol-4-yl)carbonyl]-2-piperidinyl}methyl)imidazo[1,2-a]pyrimidine; and
7-chloro-6-methyl-2-({(2S)-1-[(2-methyl-5-phenyl-1,3-thiazol-4-yl)carbonyl]-2-piperidinyl}methyl)imidazo[1,2-a]pyrimidine.

When the compound contains a $(C_{1-4})$alkyl group, whether alone or forming part of a larger group, e.g. $(C_{1-4})$alkoxy, the alkyl group may be straight chain, branched or cyclic, or combinations thereof. Examples of $(C_{1-4})$alkyl are methyl or ethyl. An example of $(C_{1-4})$alkoxy is methyloxy.

Examples of halo$(C_{1-4}$alkyl include trifluoromethyl (i.e. —$CF_3$).

Examples of $(C_{1-4})$alkoxy include methyloxy and ethyloxy.

Examples of halo$(C_{1-4})$alkoxy include trifluoromethyloxy (i.e. —$OCF_3$).

Halogen or "halo" (when used, for example, in halo($C_{1-4}$ alkyl) means fluoro, chloro, bromo or iodo.

It is to be understood that the present invention covers all combinations of particularised groups and substituents described herein above.

The compounds of formula (I) are S enantiomers. Where additional chiral centres are present in compounds of formula (I), the present invention includes within its scope all possible enantiomers and diastereoisomers, including mixtures thereof. The different isomeric forms may be separated or resolved one from the other by conventional methods, or any given isomer may be obtained by conventional synthetic methods or by stereospecific or asymmetric syntheses. The invention also extends to any tautomeric forms or mixtures thereof.

It will be understood that the invention includes pharmaceutically acceptable derivatives of compounds of formula (I) and that these are included within the scope of the invention.

Particular compounds according to the invention include those mentioned in the examples and their pharmaceutically acceptable derivatives.

As used herein "pharmaceutically acceptable derivative" includes any pharmaceutically acceptable salt, ester or salt of such ester of a compound of formula (I) which, upon administration to the recipient is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse J. Pharm. Sci (1977) 66, pp 1-19. Such pharmaceutically acceptable salts include acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, eg. as the hydrate. This invention includes within its scope stoichiometric solvates (eg. hydrates) as well as compounds containing variable amounts of solvent (eg. water).

The subject invention also includes isotopically-labeled compounds which are identical to those recited in formula (I) and following, but for the fact that one or more atoms are replaced by an atom having an atomic mass or mass number different from the atomic mass or mass number most commonly found in nature. Examples if isotopes that can be incorporated into compounds of the invention include isotopes of hydrogen, carbon, nitrogen, oxygen, fluorine, iodine and chlorine such as $^3$H, $^{11}$C, $^{14}$C, $^{18}$F, $^{123}$I or $^{125}$I.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3$H or $^{14}$C have been incorporated, are useful in drug and/or substrate tissue distribution assays. Tritiated, ie. $^3$H, and carbon-14, ie. $^{14}$C, isotopes are particularly preferred for their ease of preparation and detectability. $^{11}$C and $^{18}$F isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure fowls used in the pharmaceutical compositions.

According to a further aspect of the present invention there is provided a process for the preparation of compounds of formula (I) and derivatives thereof. The following scheme details an example of a synthetic route to compounds of the invention. In the following scheme reactive groups can be protected with protecting groups and deprotected according to well established techniques.

According to a further feature of the invention there is provided a process for the preparation of compounds of formula (I) and derivatives thereof. The following is an example of a synthetic scheme that may be used to synthesise the compounds of the invention.

Scheme

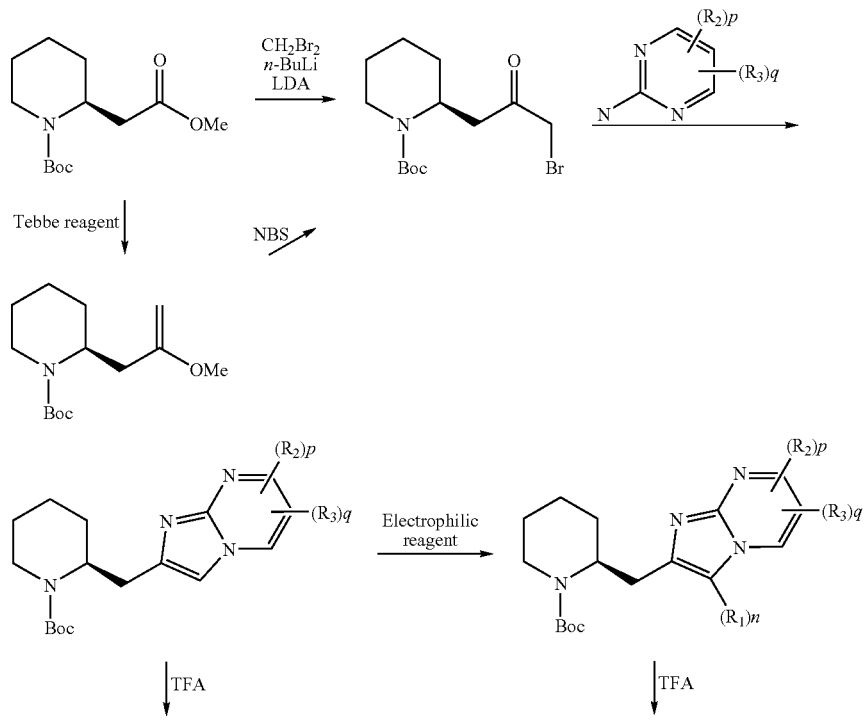

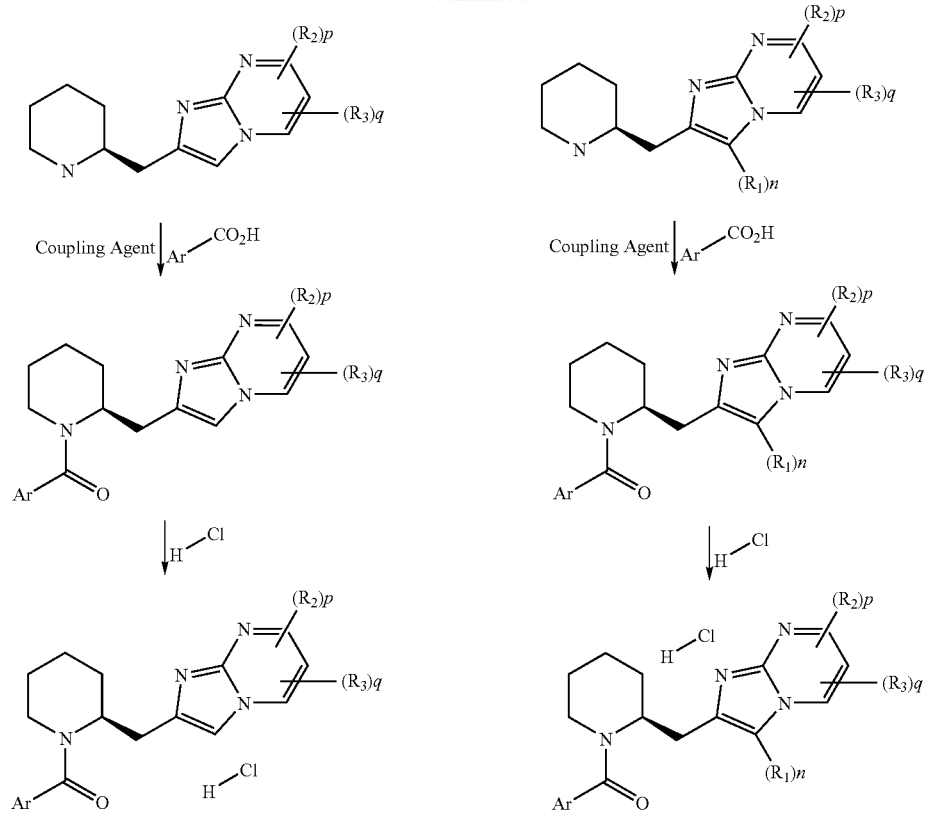

It will be understood by those skilled in the art that certain compounds of the invention can be converted into other compounds of the invention according to standard chemical methods.

The starting materials for use in the scheme are commercially available, known in the literature or can be prepared by known methods.

The compounds of formula (I) may be prepared singly or as compound libraries comprising at least 2, e.g. 5 to 1000, preferably 10 to 100 compounds of formula (I). Compound libraries may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable derivatives thereof.

Pharmaceutically acceptable salts may be prepared conventionally by reaction with the appropriate acid or acid derivative.

The present invention provides compounds of formula (I) and their pharmaceutically acceptable derivatives for use in human or veterinary medicine.

The compounds of formula (I) and their pharmaceutically acceptable derivatives are useful for the treatment of diseases or disorders where an antagonist of a human Orexin receptor is required such as obesity, including obesity observed in Type 2 (non-insulin-dependent) diabetes patients, schizophrenia, anxiety, depression, obsessive compulsive disorder, drug dependency and/or sleep disorders selected from the group consisting of dyssomnias such as primary insomnia (307.42), primary hypersomnia (307.44), narcolepsy (347), breathing-related sleep disorders (780.59), circadian rhythm sleep disorder (307.45) and dyssomnia not otherwise specified (307.47); parasomnias such as nightmare disorder (307.47), sleep terror disorder (307.46), sleepwalking disorder (307.46) and parasomnia not otherwise specified (307.47); sleep disorders related to another mental disorder such as insomnia related to another mental disorder (307.42) and hypersomnia related to another mental disorder (307.44); sleep disorder due to a general medical condition; and substance-induced sleep disorder including the subtypes insomnia type, hypersomnia type, parasomnia type and mixed type, sleep apnea and jet-lag syndrome (numbers in brackets after the listed diseases refer to the classification code in DSM-IV: Diagnostic and Statistical Manual of Mental Disorders, 4th Edition, published by the American Psychiatric Association. The various subtypes of the disorders mentioned herein are contemplated as part of the present invention).

Additionally the compounds of formula (I) and pharmaceutically acceptable derivatives are useful for the treatment of stroke, particularly ischemic or haemorrhagic and/or in blocking an emetic response i.e. nausea and vomiting.

The invention also provides a method of treating or preventing diseases or disorders where an antagonist of a human orexin receptor is required, for example those diseases and disorders mentioned hereinabove, which comprises administering to a subject in need thereof an effective amount of a compound of formula (I), or a pharmaceutically acceptable derivative thereof.

The invention also provides a compound of formula (I), or a pharmaceutically acceptable derivative thereof, for use in the treatment or prophylaxis of diseases or disorders where an antagonist of a human orexin receptor is required, for example those diseases and disorders mentioned hereinabove.

The invention also provides the use of a compound of formula (I), or a pharmaceutically acceptable derivative thereof, in the manufacture of a medicament for the treatment or prophylaxis of diseases or disorders where an antagonist of a human Orexin receptor is required, for example those diseases and disorders mentioned hereinabove.

The invention also provides the use of a compound of formula (I), or a pharmaceutically acceptable derivative thereof, in the manufacture of a medicament for the treatment or prophylaxis of diseases or disorders where an antagonist of a human Orexin receptor is required such as obesity, including obesity observed in Type 2 (non-insulin-dependent) diabetes patients, schizophrenia, anxiety, depression, obsessive compulsive disorder, drug dependency and/or sleep disorders selected from the group consisting of dyssomnias such as primary insomnia (307.42), primary hypersomnia (307.44), narcolepsy (347), breathing-related sleep disorders (780.59), circadian rhythm sleep disorder (307.45) and dyssomnia not otherwise specified (307.47); parasomnias such as nightmare disorder (307.47), sleep terror disorder (307.46), sleepwalking disorder (307.46) and parasomnia not otherwise specified (307.47); sleep disorders related to another mental disorder such as insomnia related to another mental disorder (307.42) and hypersomnia related to another mental disorder (307.44); sleep disorder due to a general medical condition; and substance-induced sleep disorder including the subtypes insomnia type, hypersomnia type, parasomnia type and mixed type, sleep apnea and jet-lag syndrome (numbers in brackets after the listed diseases refer to the classification code in DSM-IV: Diagnostic and Statistical Manual of Mental Disorders, 4th Edition, published by the American Psychiatric Association. The various subtypes of the disorders mentioned herein are contemplated as part of the present invention).

For use in therapy the compounds of the invention are usually administered as a pharmaceutical composition. The invention also provides a pharmaceutical composition comprising a compound of formula (I), or a pharmaceutically acceptable derivative thereof, and a pharmaceutically acceptable carrier.

The compounds of formula (I) and their pharmaceutically acceptable derivatives may be administered by any convenient method, e.g. by oral, parenteral, buccal, sublingual, nasal, rectal or transdermal administration, and the pharmaceutical compositions adapted accordingly.

The compounds of formula (I) and their pharmaceutically acceptable derivatives which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier (s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the limb of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable derivative thereof, used in the treatment or prophylaxis of the abovementioned disorders or diseases will vary in the usual way with the particular disorder or disease being treated, the weight of the subject and other similar factors. However, as a general rule, suitable unit doses may be 0.05 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable derivatives the above figures are calculated as the parent compound of formula (I).

No toxicological effects are indicated/expected when a compound of formula (I) is administered in the above mentioned dosage range.

Human Orexin-A has the amino acid sequence:

```
pyroGlu Pro Leu Pro Asp Cys Cys Arg Gln Lys Thr
  1               5                   10

Cys Ser Cys Arg Leu Tyr Glu Leu Leu His Gly Ala
      15                          20

Gly Asn His Ala Ala Gly Ile Leu Thr Leu-NH2
      25                30
```

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, *Drosophila* or *E. coli*. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into *Xenopus* oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor.

Throughout the specification and claims which follow, unless the context requires otherwise, the word 'comprise', and variations such as 'comprises' and 'comprising' will be understood to imply the inclusion of a stated integer or step or group of integers but not to the exclusion of any other integer or step or group of integers or steps.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The Descriptions 1 to 5 illustrate the preparation of intermediates to compounds of the invention.

In the procedures that follow, after each starting material, reference to a description is typically provided. This is provided merely for assistance to the skilled chemist. The starting material may not necessarily have been prepared from the batch referred to.

The compounds described in the Examples described hereinafter have all been prepared as a first step from stereochemically pure methyl 5-oxo-L-prolinate or ethyl 5-oxo-D-prolinate. The stereochemistry of the compounds of the Descriptions and Examples have been assigned on the assumption that the pure configuration of 5-oxo-prolinate is maintained.

Compounds are named using ACD/Name PRO 6.02 chemical naming software (Advanced Chemistry Development Inc., Toronto, Ontario, M5H2L3, Canada).

Proton Magnetic Resonance (NMR) spectra were recorded either on Varian instruments at 300, 400 or 500 MHz, or on a Bruker instrument at 300 and 400 MHz. Chemical shifts are reported in ppm (δ) using the residual solvent line as internal standard. Splitting patterns are designed as s, singlet; d, doublet; t, triplet; q, quartet; m, multiplet; b, broad.

The NMR spectra were recorded at a temperature ranging from 25 to 90° C. When more than one conformer was detected the chemical shifts for the most abundant one is reported.

HPLC analysis indicated by $R_t$(HPLC): x min, was performed on an Agilent 1100 series instrument using a Luna 3u C18(2) 100A (50×2.0 mm) column (mobile phase: 100% [water+0.05% TFA] to 95% [acetonitrile+0.05% TFA] in 8 min, flux=1 ml/min, detection wavelength 220 nm.

Mass spectra (MS) were taken on a 4 II triple quadrupole Mass Spectrometer (Micromass UK) or on a Agilent MSD 1100 Mass Spectrometer, operating in ES (+) and ES (−) ionization mode or on an Agilent LC/MSD 1100 Mass Spectrometer, operating in ES (+) and ES (−) ionization mode coupled with HPLC instrument Agilent 1100 Series [LC/MS–ES (+): analysis performed on a Supelcosil ABZ +Plus (33×4.6 mm, 3 μm) (mobile phase: 100% [water+0.1% $HCO_2H$] for 1 min, then from 100% [water+0.1% $HCO_2H$] to 5% [water+0.1% $HCO_2H$] and 95% [$CH_3CN$] in 5 min, finally under these conditions for 2 min; T=40° C.; flux=1 mL/min; LC/MS–ES(−): analysis performed on a Supelcosil ABZ+Plus (33×4.6 mm, 3 μm) (mobile phase: 100% [water+0.05% $NH_3$] for 1 min, then from 100% [water+0.05% $NH_3$ to 5% [water+0.05% $NH_3$] and 95% [$CH_3CN$] in 5 min, finally under these conditions for 2 min; T=40° C.; flux=1 mL/min]. In the mass spectra only one peak in the molecular ion cluster is reported.

For reactions involving microwave irradiation, a Personal Chemistry Emrys™ Optimizer was used.

Flash silica gel chromatography was carried out on silica gel 230-400 mesh (supplied by Merck A G Darmstadt, Germany) or over Varian Mega Be-Si pre-packed cartridges or over pre-packed Biotage silica cartridges.

SPE-SCX cartridges are ion exchange solid phase extraction columns supplied by Varian. The eluent used with SPE-SCX cartridges is methanol followed by 2N ammonia solution in methanol.

In a number of preparations, purification was performed using either Biotage manual flash chromatography (Flash+) or automatic flash chromatography (Horizon) systems. All these instruments work with Biotage Silica cartridges.

SPE-Si cartridges are silica solid phase extraction columns supplied by Varian.

The following table lists the abbreviations used in the text:

| | |
|---|---|
| AcCl | Acetyl chloride |
| BINAP | 2,2'-Bis(diphenylphosphino)-1,1'-binaphthyl |
| Boc | t-Butoxycarbonyl |
| n-BuLi | N Butyl Lithium |
| s-BuLi | Sec Butyl Lithium |
| Cy | Cyclohexanes |
| DCM | Dichloromethane |
| DIPA | N,N-diisopropylamine |
| DIPEA | N,N-diisopropyl-N-ethylamine |
| DME | 1,2-Dimethoxyethane |
| DMF | Dimethylformamide |
| $Et_2O$ | Diethylether |
| EtOAc | Ethylacetate |
| LAH | Lithium Aluminum Hydride |
| LDA | Lithiumdiisopropylamide |
| MsCl | Mesylchloride |
| NBS | N-Bromosuccinimide |
| NCS | N-Chlorosuccinimide |
| rt | Room Temperature |
| TBTU | O-(benzotriazol-1-yl)-N,N,N'N'-tetramethyluronium tetrafluoroborate |
| TEA | Triethylamine |
| TFA | Trifluoroacetic acid |
| THF | Tetrahydrofuran |

Descriptions

Description 1: 1,1-dimethylethyl (2S)-2-[2-(methyloxy)-2-oxoethyl]-1-piperidinecarboxylate (D1)

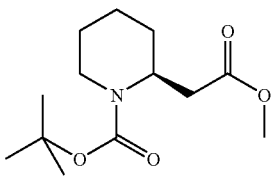

Into a 250 ml round bottom flask ((2S)-1-{[(1,1-dimethylethyl)oxy]carbonyl}-2-piperidinyl)acetic acid (1.00 g, 4.11 mmol), DMF (25 ml), DIPEA (2.15 ml, 12.33 mmol) and TBTU (1.98 g, 6.17 mmol) were added. The mixture was stirred at rt for 20 min and a brown colour was formed. After this time MeOH (0.25 ml, 6.17 mmol) was added and the resulting solution stirred at rt for 30 min. Then it was transferred into e separatory funnel containing brine (20 ml) and extracted with EtOAc (20 ml×2), the combined organic layers were washed with water/ice (5×20 ml). The organic layer was dried ($Na_2SO_4$), filtered and concentrated. The crude obtained was purified by column chromatography (Biotage SP1, Cy-EtOAc from 100/0 to 85/15). Collected fractions gave the title compound (1.01 g, 3.92 mmol, 95% yield) as a colorless oil. $^1$H-NMR (500 MHz, $CDCl_3$) δ(ppm): 4.67-4.75 (m, 1H), 3.96-4.05 (m, 1H), 3.67 (s, 3H), 2.79 (t, 1H), 2.61 (dd, 1H), 2.53 (dd, 1H), 1.60-1.70 (m, 6H), 1.46 (s, 9H).

Description 2: 1,1-dimethylethyl (2S)-2-(3-bromo-2-oxopropyl)-1-piperidinecarboxylate (D2)

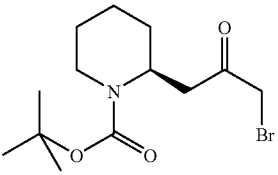

In a 500 ml round-bottomed flask under nitrogen at rt, D1 (11.1 g, 43.1 mmol) was dissolved in THF (100 ml) to give a pale yellow solution. This solution was cooled to −78° C. and the Tebbe reagent (104 ml of a 0.5 M solution in toluene, 51.8 mmol) was added dropwise. The thick mixture was diluted with further 70 ml of dry toluene. The resulting brown-orange mixture was stirred at this temperature for 30 min and then slowly warmed up to rt and left under stirring for 2 h. The reaction mixture was charged into a dropping funnel and then added dropwise to a 2 L round-bottomed flask containing ~400 ml of NaOH 1 M aqueous solution cooled at 0° C. At the end of the quench, the resulting grey suspension was diluted with EtOAc (250 ml) and allowed to stir overnight (mechanical stirring). The resulting yellow suspension was then filtered over a Gooch funnel (using Sterimat): salts were washed with EtOAc (~500 ml). Phases were then separated and the organic layer was washed with brine (2×500 ml). The combined organic phases were dried ($Na_2SO_4$), filtered and concentrated to give a deep orange oil. This material was diluted with ~500 ml of $Et_2O$: some salts precipitated, so the resulting suspension was filtered over a Gooch funnel (using Sterimat). The filtrate was concentrated under vacuum to give 12.4 g of crude 1,1-dimethylethyl (2S)-2-[2-(methyloxy)-2-propen-1-yl]-1-piperidinecarboxylate as an orange-brown oil. The material contained some residual salts (as the overall recovered amount was higher than the theoretical amount). The material was used without further purification in the next reaction and supposed to be pure at 89 wt %. In a 1 L round-bottomed flask under nitrogen at rt 1,1-dimethylethyl (2S)-2-[2-(methyloxy)-2-propen-1-yl]-1-piperidinecarboxylate (12.4 g, 43.1 mmol) was dissolved in THF (125 ml) and water (35 ml) to give a pale yellow solution. NBS (7.67 g, 43.1 mmol) was then added dissolved in ~100 ml of THF. The resulting grey mixture was stirred at rt for 1 h. Then additional NBS (0.2 eq, 1.5 g) dissolved in 50 ml of THF was added and the reaction mixture stirred at rt for 1 h. The mixture was concentrated under vacuum to remove THF, then was diluted with EtOAc (~500 ml) and water (200 ml). Phases were separated and the aqueous layer was back-extracted with EtOAc (250 ml). The combined organic layers were dried ($Na_2SO_4$) filtered and concentrated to give: 17.8 g of a brown oil. This material was purified by flash-chromatography (Biotage 75L, Cy-EtOAc from 100-0 to 90-10) to give the title compound (6.0 g, 18.7 mmol, 43% yield from D1, two steps) as a slightly yellow oil that solidified upon standing. UPLC: rt=0.79, peaks observed: 344 [M+Na, 100%], 342 [M+Na, 100%], 266 [M-tBu, 100%] and 264 [M-tBu, 100%]. $^1$H NMR (500 MHz, $CDCl_3$) δ(ppm): 4.72-4.79 (m, 1H), 3.91-4.10 (m, 3H), 2.77-2.97 (m, 3H), 1.49-1.75 (m, 6H), 1.46 (s, 9H).

Description 3: 1,1-dimethylethyl (2S)-2-[(7-methylimidazo[1,2-a]pyrimidin-2-yl)methyl]-1-piperidinecarboxylate (D3)

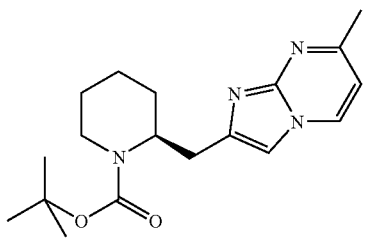

To a solution of 1,1-dimethylethyl (2S)-2-(3-bromo-2-oxopropyl)-1-piperidinecarboxylate D2 (0.300 g, 0.94 mmol) in DMF (2 ml) was added 4-methyl-2-pyrimidinamine (0.153 g, 1.41 mmol) and the mixture was stirred at 80° C. for 1.5 h. To the reaction mixture was added brine and a saturated $NaHCO_3$ aqueous solution and extracted with EtOAc. The organic layer was dried ($Na_2SO_4$), filtered and evaporated and the residue was purified by flash cromatography on silica gel (Biotage 25+M, DCM/MeOH from 100/0 to 90/10). Collected fractions gave the title compound (0.350 g slightly contaminated with residual 4-methyl-2-pyrimidinamine). UPLC: rt=0.53, peak observed: 331 (M+1). $C_{18}H_{26}N_4O_2$ requires 330.

Description 4: 1,1-dimethylethyl (2S)-2-[(3-chloro-7-methylimidazo[1,2-a]pyrimidin-2-yl)methyl]-1-piperidinecarboxylate (D4)

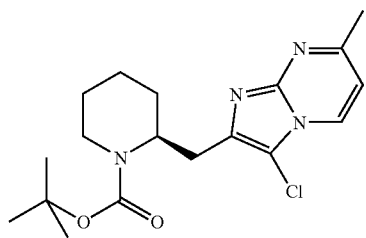

To a solution of 1,1-dimethylethyl (2S)-2-[(7-methylimidazo[1,2-a]pyrimidin-2-yl)methyl]-1-piperidinecarboxylate (0.350 g, 0.53 mmol) in DCM (5 ml) was added NCS (0.071 g, 0.53 mmol) and the reaction mixture was stirred for 1.5 h at rt. The solvent was evaporated and the residue purified by cromatography on silica gel (Biotage, NH phase 25+M, Cy/EtOAc from 100/0 to 50/50). Collected fractions gave the title compound (0.085 g, 0.23 mmol, 44% yield) as a colourless solid. UPLC: rt=0.70, peak observed: 365 (M+1, 100%) and 367 (M+1, 33%). $C_{18}H_{25}ClN_4O_2$ requires 365.

Description 5: 3-chloro-7-methyl-2-[(2S)-2-piperidinylmethyl]imidazo[1,2-a]pyrimidine (D5)

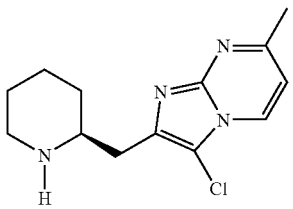

To a solution of 1,1-dimethylethyl (2S)-2-[(3-chloro-7-methylimidazo[1,2-a]pyrimidin-2-yl)methyl]-1-piperidinecarboxylate (D4) (0.085 g, 0.23 mmol) in DCM (2 ml), TFA (0.5 ml) was added dropwise at 0° C. and the solution was stirred for 1 h. The solvent was removed and the residue charged into a SCX column and eluted with methanol and ammonia 2 M in methanol. Collected fractions gave the title compound (0.060 g, 0.23 mmol, 97% yield) as a colorless oil. UPLC: rt=0.39, peak observed: 265 (M+1, 100%) and 267 (M+1, 33%). $C_{13}H_{17}ClN_4$ requires 265. $^1$H NMR (400 MHz, CDCl$_3$) δ(ppm): 8.12-8.21 (d, 1H), 6.80-6.88 (d, 1H), 3.02-3.14 (m, 2H), 2.78 2.91 (m, 2H), 2.60-2.72 (m, 4H), 1.28-1.84 (m, 6H).

EXAMPLES

Example 1

7-methyl-2-({(2S)-1-[(2-methyl-5-phenyl-1,3-thiazol-4-yl)carbonyl]-2-piperidinyl}methyl)imidazo[1,2-a]pyrimidine (HCl salt) (E1)

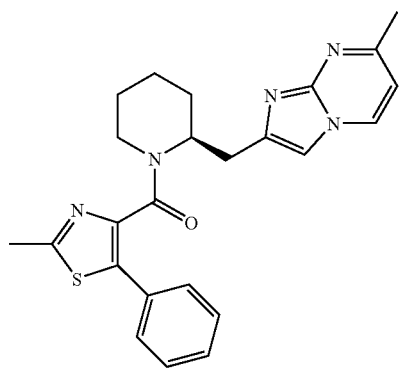

To a solution of 1,1-dimethylethyl (2S)-2-(3-bromo-2-oxopropyl)-1-piperidinecarboxylate D2 (0.215 g, 0.54 mmol) in DMF (2 ml) was added 4-methyl-2-pyrimidinamine (0.059 g, 0.54 mmol) and the mixture was stirred at 80° C. for 2.5 h. The reaction mixture was charged into a SCX column and was eluted with methanol and ammonia 2 M in methanol. Collected fractions gave 0.087 g of an oil containing a mixture of N-Boc protected 7-methyl-2-[(2S)-2-piperidinylmethyl]imidazo[1,2-a]pyrimidine and free amine contaminated with residual 4-methyl-2-pyrimidinamine. LC-MS: rt=1.43 min, m/z=331 (M+1), $C_{18}H_{26}N_4O_2$ requires 330. To a solution of this material (0.087 g) in DCM (2.5 ml), TFA (0.5 ml) was added dropwise at 0° C. and the solution was stirred for 1 h. The solvent was removed and the residue charged into a SCX column and eluted with methanol and ammonia 2 M in methanol. Collected fractions gave a crude (0.068 g) containing the free amine 7-methyl-2-[(2S)-2-piperidinylmethyl]imidazo[1,2-a]pyrimidine contaminated with residual 4-methyl-2-pyrimidinamine. MS: (ES/+) m/z: 231 [M+1]. $C_{13}H_{18}N_4$ requires 230. Into a 7 ml screw capped vial 2-methyl-5-phenyl-1,3-thiazole-4-carboxylic acid (0.036 g, 0.16 mmol) was dissolved in DCM (1 ml), Oxalyl chloride (0.031 ml, 0.36 mmol) then DMF (0.011 ml, 0.15 mmol) were added and the resulting mixture was stirred for 30 min at rt. The solvent was removed under reduced pressure and the resulting yellow solid dissolved in DCM (1 ml) and added dropwise to a solution containing 7-methyl-2-[(2S)-2-piperidinylmethyl]imidazo[1,2-a]pyrimidine (0.034 g of the crude prepared previously), and TEA (0.062 ml, 0.44 mmol) in DCM (1 ml) cooled at 0° C. The ice-bath was removed and the reaction mixture left under stirring at rt for 1 h. DCM (1 ml) was added and the mixture washed with NaHCO$_3$ (2 ml); the organic phase was separated, dried (Na$_2$SO$_4$), filtered and concentrated. The residue was purified by column chromatography on silica gel (Biotage 12 M, DCM/MeOH 98/2). The free base of the title compound (0.018 g, 0.04 mmol, 7% yield from D2, three steps) was obtained as a brown solid. UPLC: rt=0.55, peak observed: 432 (M+1). $C_{24}H_{25}N_5OS$ requires 431. $^1$H NMR [the product is present as a mixture of conformers (ratio c.ca 60/40) and the assignment refers to the single conformer] (500 MHz, CDCl$_3$) δ(ppm): 8.69 (d, 1H) 7.65 (s, 1H) 7.27-7.41 (m, 5H) 6.84 (d, 1H) 4.48 (dd, 1H) 3.85-3.93 (m, 1H) 3.01 (dt, 1H) 2.90 (dd, 1H) 2.78 (dd, 1H) 2.69 (s, 3H) 2.47 (s, 3H) 1.21-1.74 (m, 5H) 0.81-0.90 (m, 1H). The free base (0.018 g, 0.04 mmol) was transferred into a 7 ml screw capped vial with anhydrous DCM (1 ml) and the solution cooled to 0° C. HCl (0.063 ml of a 1 M solution in Et$_2$O, 0.06 mmol) was added dropwise and the mixture stirred for 15 min. The solvent was removed under reduced pressure and the resulting solid triturated with anhydrous Et$_2$O. The title compound was obtained as a light brown solid (0.019 g, 0.04 mmol, 99% yield). HPLC (walk-up): rt=3.47 min. MS: (ES/+) m/z: 432 [M+1-HCl]. C$_{24}$H$_{26}$ClN$_5$OS requires 468.

Example 2

3-chloro-7-methyl-2-({(2S)-1-[(2-methyl-5-phenyl-1,3-thiazol-4-yl)carbonyl]-2-piperidinyl}methyl)imidazo[1,2-a]pyrimidine (HCl salt) (E2)

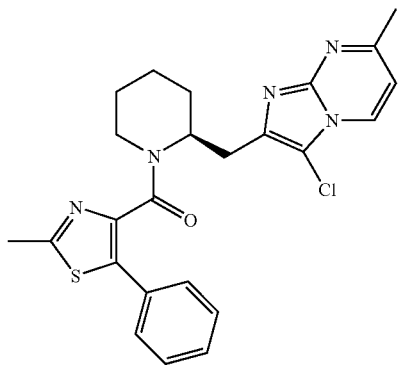

Into a 7 ml screw capped vial 2-methyl-5-phenyl-1,3-thiazole-4-carboxylic acid (0.026 g, 0.12 mmol) was dissolved in DCM (1 ml), Oxalyl chloride (0.011 ml, 0.13 mmol) then DMF (0.020 ml) were added and the resulting mixture was stirred for 1 h at rt. The solvent was removed under reduced pressure and the resulting yellow solid dissolved in DCM (1 ml) and added dropwise to a solution of 3-chloro-7-methyl-2-[(2S)-2-piperidinylmethyl]imidazo[1,2-a]pyrimidine (D5) (0.030 g, 0.11 mmol), and TEA (0.032 ml, 0.23 mmol) in DCM (1 ml) cooled at 0° C. The ice-bath was removed and the reaction mixture left under stirring at rt for 1 h. To the reaction mixture a saturated NaHCO$_3$ aqueous solution and water were added and extracted with DCM.

The organic layer was separated from the acqueous layer by separator tube and then collected and evaporated. The residue was purified by flash chromatography (Biotage NH phase 12+M, DCM/MeOH from 100/0 to 98/2). Collected fractions gave the free base of the title compound (0.027 g, 0.06 mmol, 51% yield) as a white solid. HPLC (walk-up): rt=3.95 min. UPLC: rt=0.67, peak observed: 466 (M+1, 100%) and 468 (M+1, 33%). C$_{24}$H$_{24}$ClN$_5$OS requires 466. $^1$H NMR [the product is present as a mixture of conformers (ratio c.ca 70/30)] (500 MHz, DMSO-d$^6$). The free base (0.027 g, 0.06 mmol) was dissolved in Et$_2$O/DCM (1/1) (2 ml) and HCl 1 M in Et$_2$O (1.1 eq.) was added. The resulting suspension was triturated with Et$_2$O and the solvents were evaporated affording the title compounds (0.027 g, 0.05 mmol, 47% yield) as a white solid. HPLC (walk-up): rt=3.68 min. UPLC: rt=0.67, peak observed: 466 (M+1-HCl, 100%) and 468 (M+1-HCl, 33%). C$_{24}$H$_{25}$Cl$_2$N$_5$OS requires 502.

Example 3

7-chloro-6-methyl-2-({(2S)-1-[(2-methyl-5-phenyl-1,3-thiazol-4-yl)carbonyl]-2-piperidinyl}methyl)imidazo[1,2-a]pyrimidine (HCl salt) (E3)

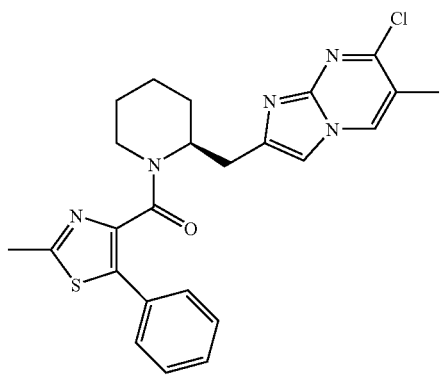

To a solution of 1,1-dimethylethyl (2S)-2-(3-bromo-2-oxopropyl)-1-piperidinecarboxylate D2 (0.100 g, 0.31 mmol) in DMF (1 ml) was added 4-chloro-5-methyl-2-pyrimidinamine (0.067 g, 0.47 mmol) and the mixture was stirred at 80° C. for 3.5 h. The reaction mixture was charged into a SCX column and was eluted with methanol and ammonia 2 M in methanol. Collected fractions gave 0.086 g of a crude containing the desired product N-Boc protected. MS: (ES/+) m/z: 366 [M+1]. C$_{18}$H$_{25}$ClN$_4$O$_2$ requires 365. To a solution o material (0.086 g) in DCM (4 ml), TFA (1 ml) was added dropwise at 0° C. and the solution was stirred for 1 h at it The solvent was removed and the residue charged into a SCX column and eluted with methanol and ammonia 2 M in methanol. Collected fractions gave a crude (0.072 g) containing the free amine 7-chloro-6-methyl-2-[(2S)-2-piperidinylmethyl]imidazo[1,2-a]pyrimidine. UPLC: rt=0.41, peak observed: 265 (M+1, 100%) and 267 (M+1, 33%). C$_{13}$H$_{17}$ClN$_4$ requires 265. Into a 7 ml screw capped vial 2-methyl-5-phenyl-1,3-thiazole-4-carboxylic acid (0.071 g, 0.33 mmol) was dissolved in DCM (1 ml), Oxalyl chloride (0.057 ml, 0.65 mmol) then DMF (one drop) were added and the resulting mixture was stirred for 30 min at rt. The solvent was removed under reduced pressure and the resulting yellow solid dissolved in DCM (1 ml) and added dropwise to the solution containing the crude (0.072 g) 7-chloro-6-methyl-2-[(2S)-2-piperidinylmethyl]imidazo[1,2-a]pyrimidine and TEA (0.113 ml, 0.81 mmol) in DCM (1 ml) cooled at 0° C. The ice-bath was removed and the reaction mixture left under stirring at rt for 2 h. DCM (1 ml) was added and the mixture washed with NaHCO$_3$ (2 ml); the organic phase was separated, dried (Na$_2$SO$_4$), filtered and concentrated. The residue was purified by Fraction Lynx (two runs) and the free base of the title compound was obtained (0.004 g, 0.001 mmol, 3% yield from D2, three steps). UPLC: rt=0.64, peak observed: 466 (M+1, 100%) and 468 (M+1, 33%). C$_{24}$H$_{24}$ClN$_5$OS requires 466. $^1$H NMR [the product is present as a mixture of conformers (ratio c.ca 60/40)] (500 MHz, DMSO-d$^6$). The free base (0.003 g, 0.0006 mmol) was transferred into a 7 ml screw capped vial with anhydrous Et$_2$O (0.2 ml) and the solution cooled to 0° C. HCl (0.14 ml of a 1 M solution in Et$_2$O, 0.14 mmol) was added dropwise and the mixture stirred for 15 min. The solvent was removed under reduced pressure and the resulting solid triturated with anhydrous Et$_2$O. The title compound was obtained (0.003 g, 0.006 mmol, 93% yield).

Example 4

Determination of Antagonist Affinity at Human Orexin-1 and 2 Receptors Using FLIPR Cell Culture Adherent Chinese Hamster Ovary (CHO) cells, stably expressing the recombinant human Orexin-1 (hOX1) or human Orexin-2 receptors (hOX2), were maintained in culture in Alpha Minimum Essential Medium (Gibco/Invitrogen, cat. no.; 22571-020), supplemented with 10% decomplemented foetal bovine serum (Life Technologies, cat. no. 10106-078) and 400 ug/mL Geneticin G418 (Calbiochem, cat. no. 345810). Cells were grown as monolayers under 95%:5% air:CO$_2$ at 37° C. and passaged every 3-4 days. The highest passage used was 25.

Measurement of [Ca$^{2+}$]$_i$ Using the FLIPR™

CHO-hOX1 or CHO-hOX2 cells were seeded into black clear-bottom 384-well plates at a density of 20,000 cells per well in culture medium as described above and maintained overnight (95%:5% air:CO$_2$ at 37° C.).

On the day of the experiment, culture medium were discarded and the cells washed three times with standard buffer (NaCl, 145 mM; KCl, 5 mM; HEPES, 20 mM; Glucose, 5.5 mM; MgCl$_2$, 1 mM; CaCl$_2$, 2 mM) added with Probenecid 2.5 mM.

The plates were then incubated at room temperature for 60 minutes in the dark with 1 μM FLUO-4AM dye to allow cell uptake of the FLUO-4AM, which is then converted by intracellular esterases to FLUO-4, which is unable to leave the cells.

After incubation, cells were washed three times with standard buffer to remove extracellular dye and 30 μL of buffer were left in each well after washing. Compounds of the invention were tested in a final assay concentration range from 1.66E-05M to 1.58E-11M.

Compounds of the invention were dissolved in dimethylsulfoxide (DMSO) at a stock concentration of 10 mM. These solutions are serially diluted with DMSO in a 384 compound plate and 1 μL of each dilution is transferred to the test compound plate. Just prior compounds addition to the cells, buffer (50 μl/well) was added to the 1 μL compound copy plate.

An agonist stimulus 384-well plate containing 50 μL/well of human orexin A (hOrexinA) was prepared just before using by diluting with buffer a stock plate: final concentration is equivalent to the calculated EC80 for hOrexinA. This value was obtained by testing hOrexinA in concentration response curve (at least 16 replicates) the same day of the experiment.

The loaded cells were then incubated for 10 min at 37° C. with test compound. The plates were then placed into a FLIPR™ (Molecular Devices, UK) to monitor cell fluorescence ($\lambda_{ex}$=488 nm, $\lambda_{EM}$=540 nm) (Sullivan E, Tucker E M, Dale I L. Measurement of [Ca$^{2+}$]; using the fluometric imaging plate reader (FLIPR). In: Lambert D G (ed.), *Calcium Signaling Protocols*. New Jersey: Humana Press, 1999, 125-136). A baseline fluorescence reading was taken over a 5 to 10 second period, and then 10 μL of EC80 hOrexinA solution was added. The fluorescence was then read over a 4-5 minute period.

Data Analysis

Functional responses using FLIPR were measured as peak fluorescence intensity minus basal fluorescence and expressed as a percentage of a non-inhibited Orexin-A-induced response on the same plate. Iterative curve-fitting and parameter estimations were carried out using a four parameter logistic model and Microsoft Excel (Bowen W P, Jerman J C. Nonlinear regression using spreadsheets. *Trends Pharmacol. Sci.* 1995; 16: 413-417). Antagonist affinity values (IC$_{50}$) were converted to functional pK$_i$ values using a modified Cheng-Prusoff correction (Cheng Y C, Prusoff W H. Relationship between the inhibition constant (K$_i$) and the concentration of inhibitor which causes 50 percent inhibition (IC$_{50}$) of an enzymatic reaction. *Biochem. Pharmacol.* 1973, 22: 3099-3108).

$$fpKi = -\log\frac{(IC_{50})}{\left(2+\left(\frac{[\text{agonist}]}{(EC_{50})}\right)^n\right)^{1/n} - 1}$$

Where [agonist] is the agonist concentration, EC$_{50}$ is the concentration of agonist giving 50% activity derived from the agonist dose response curve and n=slope of the dose response curve. When n=1 the equation collapses to the more familiar Cheng-Prusoff equation.

Compounds of the Examples tested according to this method had fpKi values in the range from 8.1 to 9.6 at the human cloned orexin-1 receptor and from 6.3 to 7.9 at the human cloned orexin-2 receptor.

The invention claimed is:
1. A compound of formula (I)

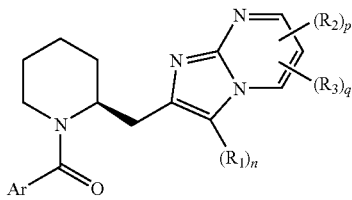

where Ar is selected from the group consisting of formula:

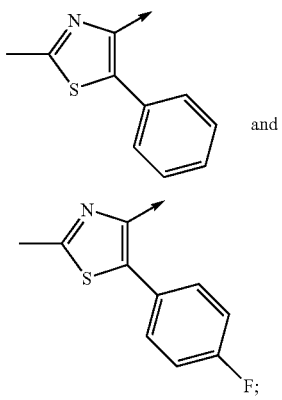

$R_1$ is $(C_{1-4})$alkyl, halo, halo$(C_{1-4})$alkyl, $(C_{1-4})$alkoxy, halo$(C_{1-4})$alkoxy, $(C_{1-4})$alkyl-O—$(C_{1-4})$alkyl, CN, $NR^5R^6$ wherein $R^5$ is H or $(C_{1-4})$alkyl and $R^6$ is H or $(C_{1-4})$alkyl;
$R_2$ is $(C_{1-4})$alkyl, halo, halo$(C_{1-4})$alkyl, $(C_{1-4})$alkoxy, halo$(C_{1-4})$alkoxy, $(C_{1-4})$alkyl-O—$(C_{1-4})$alkyl, CN, $NR^7R^8$ wherein $R^7$ is H or $(C_{1-4})$-alkyl and $R^8$ is H or $(C_{1-4})$-alkyl;
$R_3$ is $(C_{1-4})$alkyl, halo, halo$(C_{1-4})$alkyl, $(C_{1-4})$alkoxy, halo$(C_{1-4})$alkoxy, $(C_{1-4})$alkyl-O—$(C_{1-4})$alkyl, CN, $NR^9R^{10}$ wherein $R^9$ is H or $(C_{1-4})$-alkyl and $R^{10}$ is H or $(C_{1-4})$-alkyl;
n is 0 or 1;
p is 0 or 1; and
q is 0 or 1;
with the proviso that p and q are not both 0;
or a pharmaceutically acceptable salt thereof.

2. The compound, or pharmaceutically acceptable salt thereof, according to claim 1, wherein Ar is a group of formula (II), n is 1 and $R_1$ is halogen.

3. The compound, or pharmaceutically acceptable salt thereof, according to claim 1, wherein Ar is a group of formula (II), n is 1 and $R_1$ is chlorine.

4. The compound, or pharmaceutically acceptable salt thereof, according to claim 1, wherein Ar is a group of formula (II), n is 1, p is 1, q is 0, $R_1$ is chlorine and $R_2$ is methyl.

5. The compound, or pharmaceutically acceptable salt thereof, according to claim 1, wherein Ar is a group of formula (II), n is 0, p is 1, q is 0 and $R_2$ is methyl.

6. The compound, or pharmaceutically acceptable salt thereof, according to claim 1, wherein Ar is a group of formula (II), n is 0, p is 1, q is 1 and one of $R_2$ and $R_3$ is halo and the other is $(C_{1-4}$-alkyl.

7. The compound, or pharmaceutically acceptable salt thereof, according to claim 1, wherein Ar is a group of formula (II), n is 0, p is 1, q is 1, $R_2$ is halo and $R_3$ is $(C_{1-4})$-alkyl.

8. The compound, or pharmaceutically acceptable salt thereof, according to claim 1, wherein Ar is a group of formula (II), n is 0, p is 1, q is 1, $R_2$ is chloro and $R_3$ is methyl.

9. The compound, or pharmaceutically acceptable salt thereof, according to claim 1, wherein Ar is a group of formula (III), n is 1 and $R_1$ is halogen.

10. The compound, or pharmaceutically acceptable salt thereof, according to claim 1, wherein Ar is a group of formula (III), n is 1 and $R_1$ is chlorine.

11. The compound, or pharmaceutically acceptable salt thereof, according to claim 1, wherein Ar is a group of formula (III), n is 1, p is 1, q is 0, $R_1$ is chlorine and $R_2$ is methyl.

12. The compound, or pharmaceutically acceptable salt thereof, according to claim 1, wherein Ar is a group of formula (III), n is 0, p is 1, q is 0 and $R_2$ is methyl.

13. The compound, or pharmaceutically acceptable salt thereof, according to claim 1, wherein Ar is a group of formula (III), n is 0, p is 1, q is 1 and one of $R_2$ and $R_3$ is halo and the other is $(C_{1-4}$-alkyl.

14. The compound, or pharmaceutically acceptable salt thereof, according to claim 1 wherein Ar is a group of formula (III), n is 0, p is 1, q is 1, $R_2$ is halo and $R_3$ is $(C_{1-4})$-alkyl.

15. The compound, or pharmaceutically acceptable salt thereof, according to claim 1, wherein Ar is a group of formula (III), n is 0, p is 1, q is 1, $R_2$ is chloro and $R_3$ is methyl.

16. A compound which is:
7-methyl-2-({(2S)-1-[(2-methyl-5-phenyl-1,3-thiazol-4-yl)carbonyl]-2-piperidinyl}methyl)imidazo[1,2-a]pyrimidine;
3-chloro-7-methyl-2-({(2S)-1-[(2-methyl-5-phenyl-1,3-thiazol-4-yl)carbonyl]-2-piperidinyl}methyl)imidazo[1,2-a]pyrimidine;
7-chloro-6-methyl-2-({(2S)-1-[(2-methyl-5-phenyl-1,3-thiazol-4-yl)carbonyl]-2-piperidinyl}methyl)imidazo[1,2-a]pyrimidine;
or a pharmaceutically acceptable salt thereof.

17. A pharmaceutical composition comprising a) the compound, or pharmaceutically acceptable salt thereof, as defined in claim 1, and b) a pharmaceutically acceptable carrier.

* * * * *

SEQUENCE LISTING

<160> NUMBER OF SEQ ID NOS: 1

<210> SEQ ID NO 1
<211> LENGTH: 33
<212> TYPE: PRT
<213> ORGANISM: Homo sapien

<400> SEQUENCE: 1

Glu Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu